United States Patent
Hu et al.

(10) Patent No.: US 9,250,173 B2
(45) Date of Patent: Feb. 2, 2016

(54) IDENTIFYING POTENTIAL FRACTURE TREATMENT LOCATIONS IN A FORMATION BASED ON PRODUCTION POTENTIAL

(71) Applicant: Halliburton Energy Services, Inc., Houston, TX (US)

(72) Inventors: Dandan Hu, Houston, TX (US); Syed Muhammad Farrukh Hamza, Humble, TX (US); Gang Li, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 78 days.

(21) Appl. No.: 14/015,746

(22) Filed: Aug. 30, 2013

(65) Prior Publication Data

US 2015/0063650 A1 Mar. 5, 2015

(51) Int. Cl.
| | |
|---|---|
| *G06K 9/00* | (2006.01) |
| *G01N 9/00* | (2006.01) |
| *G01N 33/24* | (2006.01) |
| *G06T 17/05* | (2011.01) |
| *E21B 49/00* | (2006.01) |
| *E21B 49/02* | (2006.01) |

(52) U.S. Cl.
CPC *G01N 9/00* (2013.01); *E21B 49/00* (2013.01); *E21B 49/02* (2013.01); *G01N 33/24* (2013.01); *G01N 33/241* (2013.01); *G06K 9/00* (2013.01); *G06T 17/05* (2013.01)

(58) Field of Classification Search
USPC .............................................. 382/108, 109
See application file for complete search history.

(56) References Cited

U.S. PATENT DOCUMENTS

| | | | | |
|---|---|---|---|---|
| 5,519,793 | A * | 5/1996 | Grannes | 382/266 |
| 2003/0205658 | A1* | 11/2003 | Voisin | 249/187.1 |
| 2010/0128933 | A1* | 5/2010 | Derzhi et al. | 382/109 |
| 2010/0155078 | A1* | 6/2010 | Walters et al. | 166/369 |
| 2010/0161302 | A1* | 6/2010 | Walters et al. | 703/12 |
| 2010/0218946 | A1* | 9/2010 | Symington et al. | 166/272.6 |
| 2012/0033896 | A1* | 2/2012 | Barrows | 382/295 |
| 2012/0275658 | A1* | 11/2012 | Hurley et al. | 382/109 |
| 2012/0277996 | A1* | 11/2012 | Hurley et al. | 702/11 |
| 2013/0156270 | A1* | 6/2013 | Ellington et al. | 382/109 |
| 2014/0044315 | A1* | 2/2014 | Derzhi et al. | 382/109 |
| 2014/0157870 | A1* | 6/2014 | Kornacki et al. | 73/23.38 |

OTHER PUBLICATIONS

Slatt, R.M., et al., "Pore-to-regional-scale Integrated Characterization Workflow for Unconventional Gas Shales," The American Association of Petroleum Geologists, 2011, 26 pages.

(Continued)

*Primary Examiner* — Alex Liew
(74) *Attorney, Agent, or Firm* — Holly Soehnge; Fish & Richardson P.C.

(57) ABSTRACT

The present disclosure relates to identifying potential fracture treatment locations in a rock formation for oil and/or gas production based on production potential. One example method includes receiving internal imaging data of a core sample of a rock formation; generating a digital core sample model of the structure of the core sample based on the internal imaging data; analyzing the core sample model to determine the density distribution of a deposit in the core sample; and determining a production potential value from the density distribution of the deposit.

17 Claims, 3 Drawing Sheets

(56) References Cited

OTHER PUBLICATIONS

Jarvie, Daniel M., et al., "Unconventional shale-gas systems: The Mississippian Barnett Shale of north-central Texas as one model for thermogenic shale-gas assessment," The American Association of Petroleum Geologists, AAPG Bulletin, V. 91, No. 4 (Apr. 2007), pp. 475-499, 25 pages.

Curtis, M.E., et al., "Structural Characterization of Gas Shales on the Micro- and Nano-Scales," CUSG/SPE 137693, Canadian Unconventional Resources & International Petroleum Conference, Calgary, Alberta, Canada, Oct. 19-21, 2010, 15 pages.

Buller, Dan, et al., "Petrophysical Evaluation for Enhancing Hydraulic Stimulation in Horizontal Shale Gas Wells," SPE 132990, SPE Annual Technical Conference and Exhibition, Florence, Italy, Sep. 19-22, 2010, 21 pages.

* cited by examiner

IDENTIFYING POTENTIAL FRACTURE TREATMENT LOCATIONS IN A FORMATION BASED ON PRODUCTION POTENTIAL

BACKGROUND

This specification relates to identifying potential fracture treatment locations in a rock formation for oil and/or gas production based on production potential.

Deposits that correlate to oil and/or gas production potential may be deposited in various locations throughout a rock formation. The deposits may be of varying sizes and may occur at different frequencies in different parts of the formation. Producing oil and/or gas from the formation may involve choosing a "sweet spot" in the formation to produce from in an attempt to maximize the production and, thus, maximize profits.

DESCRIPTION OF DRAWINGS

Like reference symbols in the various drawings indicate like elements.

DETAILED DESCRIPTION

Figure 1A:
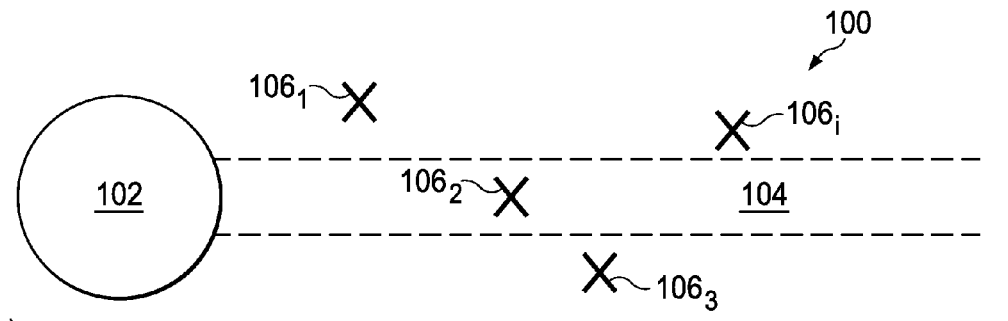
FIG. 1A a top view of an example well site.

The present disclosure describes a process for identifying potential fracture locations in a rock formation based on production potential.

In exploiting an oil and/or gas field, one or more core wells may be drilled into a rock formation from which one or more core samples may be extracted. The locations from which these core samples are extracted may be chosen based on one or more possible drilling locations and may be taken in number and distribution to provide a useful information on the formation. The one or more core samples may then be imaged using a non-destructive two dimensional (2D) and/or three-dimensional (3D) imaging technique operable to show the internal details of the core sample, such as, for example, Nuclear Magnetic Resonance (NMR), X-ray Tomography, Computerized Tomography (CT), or Focused Ion Beam Scanning Electron Microscopy (FIB-SEM) and/or other technique. Generally, the image data produced by these techniques will be raw data representing the density of the core sample in 3D space. The image data may then be analyzed to generate a digital core sample model of the structure of the core sample. In some implementations, analyzing the image data to generate the digital core sample model includes setting a range of densities that represent different types of structures within the core sample. For example, density values from X to $X^1$ may represent a rock structure such as, for example, shale, while density values from Y to $Y^1$ may represent a deposit within the rock structure, such as, for example, kerogen. Shale may considered to be a stratified sedimentary rock which is formed party or wholly from mud or clay. Mud or clay may or may not be the largest constituent of the rock sample.

The digital core sample model may then be analyzed to determine a density distribution of a deposit in the core sample. For example, in a given core sample, a density distribution for a type of deposit may be determined by quantifying the regions in the core sample containing that type of deposit according to their frequency, total volume, and largest isolated volume. In another example, in a shale core sample, a kerogen density distribution may be determined by quantifying the regions of kerogen in the core sample according to their frequency, total volume, and largest isolated volume. A production potential value may then be determined from the density distribution by taking into account weighting factors associated with the rock type and determined from macroscopic field testing. The weighting factors may be determined by performing geomechanics and associated laboratory/field tests to allow better rock characterization. For example, production potential value from a brittle rock is different than from a ductile rock. Example tests would include uniaxial compression/tensile test, triaxial compression test, direct shear test, fracture toughness test etc. In addition, customized tests based on similar principles may be carried out.

By comparing the production potential values of different core samples taken from different areas of the formation, the operator may obtain a clearer picture of the formation, and choose areas of the formation to produce from accordingly.

The foregoing approach has several potential advantages. By predicting the production potential of different areas of the formation, an operator can, in certain instances, minimize the costs associated with production by producing from fewer areas of the formation, as the operator may be able to discern which areas will provide the best return on investment for production. In addition, by taking into account not only the total volume of deposits, but also the number of deposits and the largest diameter deposit, the approach, in certain instances, may accurately quantify the production potential of various areas of the formation. Stimulation treatment of the formation may be customized depending on the production potential value at different locations in the formation. For example, the treatment can be implemented to produce a variation in spacing between different fracturing stages and/or skipping one or more stages altogether to better align the fractures with locations of high production potential.

FIG. 1A a top view of an example well site 100 including a well 102 and a horizontal leg 104 of the well 102. A series of core positions $106_1$ through $106_i$ are distributed around the horizontal leg 104. A well operator may drill cores at core locations $106_1$ through $106_i$ and/or other locations in order to assess the structure of the rock surrounding the well 102.

Figure 1B:
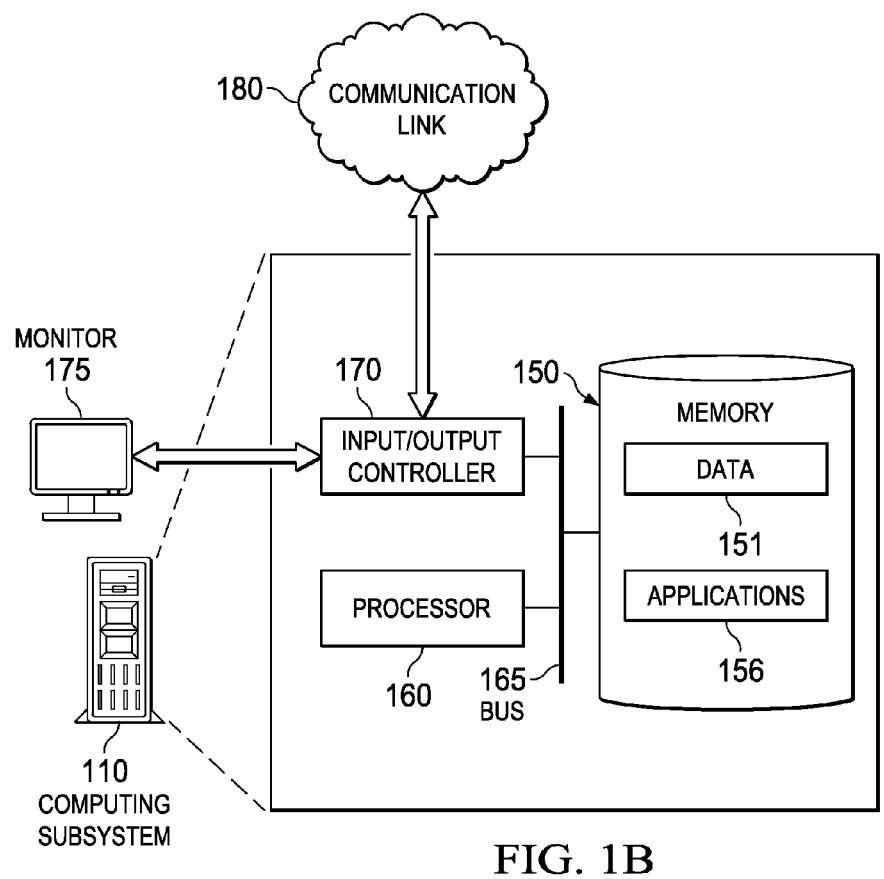
FIG. 1B is a diagram of an example computing subsystem.

FIG. 1B is a diagram of the example computing subsystem 110. The example computing subsystem 110 can be located at or near one or more wells of a well system or at a remote location. All or part of the computing subsystem 110 may operate independent of the well system. The example computing subsystem 110 includes a processor 160, a memory 150, and input/output controllers 170 communicably coupled by a bus 165. The memory can include, for example, a random access memory (RAM), a storage device (e.g., a writable read-only memory (ROM) or others), a hard disk, or another type of storage medium. The computing subsystem 110 can be preprogrammed or it can be programmed (and reprogrammed) by loading a program from another source (e.g., from a CD-ROM, from another computer device through a data network, or in another manner). The input/output controller 170 is coupled to input/output devices (e.g., a monitor 175, a mouse, a keyboard, or other input/output devices) and to a communication link 180. The input/output devices receive and transmit data in analog or digital form over communication links such as a serial link, a wireless link (e.g., infrared, radio frequency, or others), a parallel link, or another type of link.

The communication link 180 can include any type of communication channel, connector, data communication network, or other link. For example, the communication link 180 can include a wireless or a wired network, a Local Area Network (LAN), a Wide Area Network (WAN), a private network, a public network (such as the Internet), a WiFi network, a network that includes a satellite link, or another type of data communication network.

The memory 150 can store instructions (e.g., computer code) associated with an operating system, computer applications, and other resources. The memory 150 can also store application data and data objects that can be interpreted by one or more applications or virtual machines running on the computing subsystem 110. As shown in FIG. 1B, the example memory 150 includes data 151 and applications 156.

In some implementations, the data 151 stored in the memory 150 may include core model data produced by the computing system analyzing core samples taken from the subterranean zones of a formation. Such core model data may include three-dimensional models of the structure of the core samples.

The applications 156 can include software applications, scripts, programs, functions, executables, or other modules that are interpreted or executed by the processor 160. Such applications may include machine-readable instructions for performing one or more of the operations represented in FIG. 3. The applications 156 may include machine-readable instructions for determining a production potential value, as shown in the remaining FIGS. The applications 156 can obtain input data from the memory 150, from another local source, or from one or more remote sources (e.g., via the communication link 180). The applications 156 can generate output data and store the output data in the memory 150, in another local medium, or in one or more remote devices (e.g., by sending the output data via the communication link 180).

The processor 160 can execute instructions, for example, to generate output data based on data inputs. For example, the processor 160 can run the applications 156 by executing or interpreting the software, scripts, programs, functions, executables, or other modules contained in the applications 156. The processor 160 may perform one or more of the operations represented in FIG. 3. The input data received by the processor 160 or the output data generated by the processor 160 can include any of the data 151.

Figure 2A:
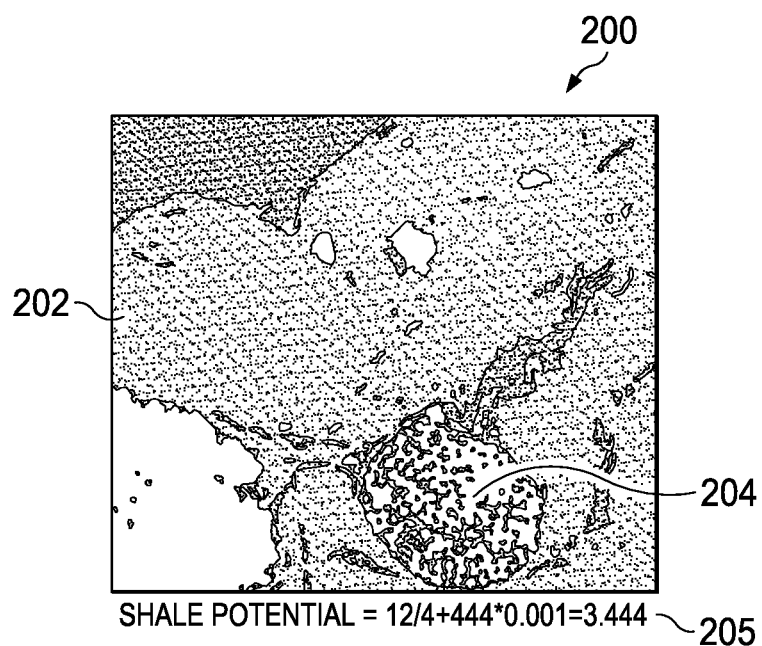
FIG. 2A is an internal image of a formation showing a distribution of deposits.

FIG. 2A is an internal image of a core sample 200 showing a distribution of deposits. As shown, the internal image of the core sample 200 includes rock 202 and deposits 204. As previously discussed, the internal image may be raw imaging data indicating densities at different locations in the core sample 200. Ranges for this density may be chosen such that structures having a density within a first range are considered rock structures, and structures having a density within a second range are considered deposits. For example, density values from X to $X^1$ may represent shale, while density values from Y to $Y^1$ may represent kerogen deposits. In some implementations, there may be multiple ranges of densities representing different types of structures.

In the illustrated implementation, the core sample 200 is taken from a shale formation and is being used to quantify the density distribution of kerogen in the formation. The core sample 200 may also be taken from any other type of formation, and may be used to quantify the density distribution of any type of deposit, including, but not limited to, pyrite, clay, quartz, calcite, or any other type of deposit.

As shown, the core sample 200 includes rock 202 and one or more deposits 204. The core sample 200 may be analyzed as discussed previously to determine the production potential value. In the illustrated implementation, a shale potential value 205 of 3.444 has been computed for the core sample 200. As previously discussed, in some implementations, the shale potential value may be computed according to the following formula:

$$P_p = w_1 * \frac{f(m_t)}{f(m_i)} + w_2 * (m_{ld})$$

where $P_p$ is production potential value, $m_t$ is total volume, $m_i$ is number of isolated deposits, $m_{ld}$ is the largest diameter of isolated volume, $w_1$ and $w_2$ are weighting factors and $f(x)$ denotes some function of x. The function denotes may be a simple numerical representation of the volume or quantity of the identified structure. In other instances, it may be a linear, quadratic or higher order polynomial or trigonometric or differential expression to quantify the structures in the imaging data.

Figure 2B:
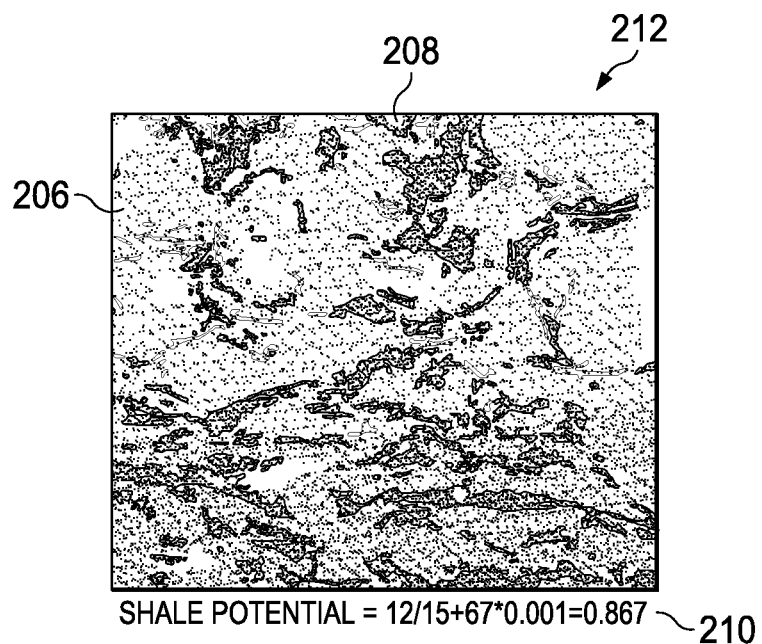
FIG. 2B an internal image of a formation showing another distribution of deposits.

FIG. 2B is an internal image of a core sample 212 showing another distribution of deposits. The core sample 212 includes rock 206 and deposits 208. Again, the core sample 212 is taken from a shale formation and is being used to quantify the density distribution of kerogen in the formation, so the deposits 208 are kerogen deposits. The shale potential value 210 for the core sample 212 has been computed to be 0.867, indicating that the core sample 212 has a lesser production potential than the core sample 200. The production potential of the core sample 212 is lower than the core sample 200 because it has less potential to be stimulated by hydraulic fracturing and subsequently produce oil and gas.

Figure 3:
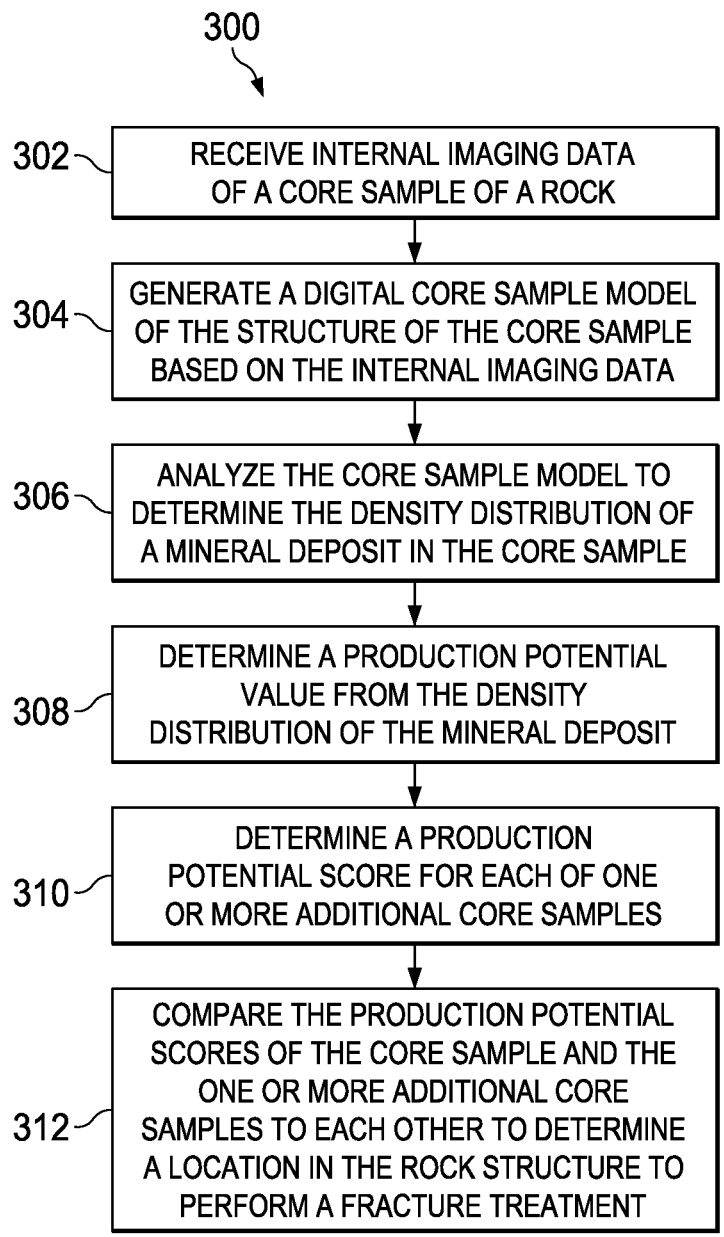
FIG. 3 is a flow chart illustrating an example method for identifying potential fracture treatment locations in a rock formation during oil and gas exploration based on production potential.

FIG. 3 is a flow chart illustrating an example method for identifying fracture locations in a rock formation. At 302, internal imaging data of a core sample of a rock is received. In some implementations, the internal imaging data is raw image data. The internal imaging data may indicate relative densities at different locations within the core sample. In some cases, the internal imaging data may be produced by imaging the core sample with a 3D imaging technique, such as, for example, NMR, FIB-SEM, X-ray Tomography, and/or another imaging technique.

At 304, a digital core sample model of the structure of the core sample is generated based on the internal imaging data. As previously discussed, the digital core sample model may identify different structures within the core sample, such as rock structures and deposits. In some implementations, the digital core sample model may be generated by assigning density ranges to different types of structures, and characterizing the structures from the image data based on these densities.

At 306, the core sample model is analyzed to determine the density distribution of the deposit in the core sample. As previously discussed, the total volume of the deposit, the total number of isolated volumes, and the largest diameter of isolated volume may be used in determining the density distribution of the deposit.

At 308, a production potential value is determined from the density distribution of the deposit. As previously discussed, the production potential value may be determined according to the following formula:

$$P_p = w_1 * \frac{f(m_t)}{f(m_i)} + w_2 * (m_{ld})$$

where $P_p$ is production potential, $m_t$ is total volume, $m_i$ is number of isolated deposits, $m_{ld}$ is the largest diameter of isolated volume, $w_1$ and $w_2$ are weighting factors and f(x) denotes some function of x.

At 310, a production potential score is determined for each of one or more additional core samples. In some implementations, the additional core samples may be taken from different areas of the same formation as the core sample, or maybe taken from different formations.

At 312, the production potential scores of the core sample and the one or more additional core samples are compared to each other to determine a location or locations in the rock formation to perform a fracture treatment. In some implementations, the fracture locations may be specific locations along the length of the well, and may be one or more than one fracture locations for a given well or for multiple wells. In some cases, a fracture treatment may be applied to the fracture locations based on the determination at 312.

Although the concepts of the present disclosure are generally described in the context of fracturing treatments, the concepts are relevant to locating other types of well treatments. In addition, the concepts herein are also relevant to the placement of well bores.

Embodiments of subject matter and operations described in this specification can be implemented in digital electronic circuitry, or in computer software, firmware, or hardware, including the structures disclosed in this specification and their structural equivalents, or in combinations of one or more of them. Some embodiments of subject matter described in this specification can be implemented as one or more computer programs, i.e., one or more modules of computer program instructions, encoded on computer storage medium for execution by, or to control the operation of, data processing apparatus. A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Some of the processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and processors of any kind of digital computer. Generally, a processor will receive instructions and data from a read only memory or a random access memory or both. A computer includes a processor for performing actions in accordance with instructions and one or more memory devices for storing instructions and data. A computer may also include, or be operatively coupled to receive data from or transfer data to, or both, one or more mass storage devices for storing data, e.g., magnetic, magneto optical disks, or optical disks. However, a computer need not have such devices. Devices suitable for storing computer program instructions and data include all forms of non-volatile memory, media and memory devices, including by way of example semiconductor memory devices (e.g., EPROM, EEPROM, flash memory devices, and others), magnetic disks (e.g., internal hard disks, removable disks, and others), magneto optical disks, and CD ROM and DVD-ROM disks. The processor and the memory can be supplemented by, or incorporated in, special purpose logic circuitry.

To provide for interaction with a user, operations can be implemented on a computer having a display device (e.g., a monitor, or another type of display device) for displaying information to the user and a keyboard and a pointing device (e.g., a mouse, a trackball, a tablet, a touch sensitive screen, or another type of pointing device) by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

A client and server are generally remote from each other and typically interact through a communication network. Examples of communication networks include a local area network ("LAN") and a wide area network ("WAN"), an inter-network (e.g., the Internet), a network comprising a satellite link, and peer-to-peer networks (e.g., ad hoc peer-to-peer networks). The relationship of client and server arises by virtue of computer programs running on the respective computers and having a client-server relationship to each other.

In some aspects, some or all of the features described here can be combined or implemented separately in one or more software programs. The software can be implemented as a computer program product, an installed application, a client-server application, an Internet application, or any other suitable type of software While this specification contains many details, these should not be construed as limitations on the scope of what may be claimed, but rather as descriptions of features specific to particular examples. Certain features that are described in this specification in the context of separate implementations can also be combined. Conversely, various features that are described in the context of a single implementation can also be implemented in multiple embodiments separately or in any suitable subcombination.

A number of embodiments have been described. Nevertheless, it will be understood that various modifications can be made. Accordingly, other embodiments are within the scope of the following claims.

The invention claimed is:

1. A computer-implemented method executed by one or more processors, the method comprising:
   receiving internal imaging data of a core sample of a rock formation;
   generating, by the one or more processors, a digital core sample model of the structure of the core sample based on the internal imaging data;
   analyzing, by the one or more processors, the core sample model to determine the density distribution of a deposit in the core sample based at least in part on a total volume of the deposit within the core sample;
   determining, by the one or more processors, a production potential value from the density distribution of the deposit; and
   determining a production potential score for each of one or more additional core samples from different locations in the rock formation;
   comparing the production potential scores of the core sample and the one or more additional core samples to each other; and
   determining a location in the rock to perform a fracture treatment based on the comparison of the production potential scores.

2. The method of claim 1, wherein the rock is shale and the density distribution of the deposit includes a density distribution of kerogen.

3. The method of claim 2, wherein the production potential value includes a shale potential value representing a ratio of a total kerogen content of the core sample to a number of isolated kerogen volumes in the core sample added to a largest diameter isolated kerogen volume in the core sample.

4. The method of claim 1, wherein the density distribution of the deposit includes a density distribution of at least one of: pyrite, clay, quartz, or calcite.

5. The method of claim 1, wherein imaging the core sample is performed using a non-destructive, three-dimensional imaging technique.

6. The method of claim 5, wherein the three-dimensional imaging technique includes at least one of: focused ion beam-scanning electron microscopy (FIB-SEM), computerized tomography (CT), X-ray tomography, or nuclear magnetic resonance (NMR).

7. A system comprising:
   memory for storing data; and
   one or more processors operable to perform operations comprising:
      receiving internal imaging data of a core sample of a rock formation;
      generating, by the one or more processors, a digital core sample model of the structure of the core sample based on the internal imaging data;
      analyzing, by the one or more processors, the core sample model to determine the density distribution of a deposit in the core sample based at least in part on a total volume of the deposit within the core sample;
      determining, by the one or more processors, a production potential value from the density distribution of the deposit; and
      determining a production potential score for each of one or more additional core samples from different locations in the rock formation;
      comparing the production potential scores of the core sample and the one or more additional core samples to each other; and
      determining a location in the rock to perform a fracture treatment based on the comparison of the production potential scores.

8. The system of claim 7, wherein the rock is shale and the density distribution of the deposit includes a density distribution of kerogen.

9. The system of claim 8, wherein the production potential value includes a shale potential value representing a ratio of a total kerogen content of the core sample to a number of isolated kerogen volumes in the core sample added to a largest diameter isolated kerogen volume in the core sample.

10. The system of claim 7, wherein the density distribution of the deposit includes a density distribution of at least one of: pyrite, clay, quartz, or calcite.

11. The system of claim 7, wherein imaging the core sample is performed using a non-destructive, three-dimensional imaging technique.

12. The system of claim 11, wherein the three-dimensional imaging technique includes at least one of: focused ion beam-scanning electron microscopy (FIB-SEM), computerized tomography (CT), X-ray tomography, or nuclear magnetic resonance (NMR).

13. A tangible, non-transitory storage medium encoded with computer-readable instructions for causing one or more processors to perform operations comprising:
   receiving internal imaging data of a core sample of a rock formation;
   generating, by the one or more processors, a digital core sample model of the structure of the core sample based on the internal imaging data;
   analyzing, by the one or more processors, the core sample model to determine the density distribution of a deposit in the core sample based at least in part on a total volume of the deposit within the core sample;
   determining, by the one or more processors, a production potential value from the density distribution of the deposit; and
   determining a production potential score for each of one or more additional core samples from different locations in the rock formation;
   comparing the production potential scores of the core sample and the one or more additional core samples to each other; and
   determining a location in the rock to perform a fracture treatment based on the comparison of the production potential scores.

14. The storage medium of claim 13, wherein the rock is shale and the density distribution of the deposit includes a density distribution of kerogen.

15. The storage medium of claim 14, wherein the production potential value includes a shale potential value representing a ratio of a total kerogen content of the core sample to a number of isolated kerogen volumes in the core sample added to a largest diameter isolated kerogen volume in the core sample.

16. The storage medium of claim 13, wherein the density distribution of the deposit includes a density distribution of at least one of: pyrite, clay, quartz, or calcite.

17. The storage medium of claim 13, wherein imaging the core sample is performed using a non-destructive, three-dimensional imaging technique.

* * * * *